US006925145B2

(12) United States Patent
Batzinger et al.

(10) Patent No.: US 6,925,145 B2
(45) Date of Patent: Aug. 2, 2005

(54) HIGH SPEED DIGITAL RADIOGRAPHIC INSPECTION OF PIPING

(75) Inventors: Thomas J. Batzinger, Burnt Hills, NY (US); Brian W. Lasiuk, Niskayuna, NY (US); Peter Allison, Conroe, TX (US); Gregory A. Mohr, Scotia, NY (US); August D. Matula, Fredericksburg, VA (US)

(73) Assignee: General Electric Company, Fairfield, CT (US)

( * ) Notice: Subject to any disclaimer, the term of this patent is extended or adjusted under 35 U.S.C. 154(b) by 0 days.

(21) Appl. No.: 10/646,279

(22) Filed: Aug. 22, 2003

(65) Prior Publication Data

US 2005/0041775 A1 Feb. 24, 2005

(51) Int. Cl.⁷ .................................................. G01B 15/06
(52) U.S. Cl. .............................................. 378/59; 378/4
(58) Field of Search ........................... 378/4–20, 58–60, 378/198

(56) References Cited

U.S. PATENT DOCUMENTS

| | | | |
|---|---|---|---|
| 4,725,963 A | 2/1988 | Taylor et al. | |
| 4,982,415 A | 1/1991 | Shibata et al. | |
| 5,014,293 A | * 5/1991 | Boyd et al. | 378/197 |
| 5,420,427 A | * 5/1995 | Morgan et al. | 250/360.1 |
| 5,614,720 A | 3/1997 | Morgan et al. | |
| 5,698,854 A | 12/1997 | Gupta | |
| 6,154,516 A | 11/2000 | Heuscher et al. | |
| 6,459,760 B1 | 10/2002 | D'Ambrosio | |
| 6,466,643 B1 | 10/2002 | Bueno et al. | |
| 6,507,635 B2 | 1/2003 | Birdwell et al. | |
| 2002/0181650 A1 | 12/2002 | D'Ambrosio et al. | |

FOREIGN PATENT DOCUMENTS

| | | |
|---|---|---|
| EP | 0710834 A1 | 8/1996 |
| JP | 09304303 | 11/1997 |

OTHER PUBLICATIONS

Walker, Stan M., US13 New NDE Developments Support Rapid, Economical Screening For Flow–Accelerated Corrosion; EPRI NDE Center, 1300 Harris Blvd., Charlotte, NC 28262, Oct. 1999, vol. 4. No. 10.

* cited by examiner

Primary Examiner—Craig E. Church
Assistant Examiner—Jurie Yun
(74) Attorney, Agent, or Firm—Wegman Hessler & Vanderburg

(57) ABSTRACT

A system and method for high-speed radiographic inspection of fluid transport vessels in which a radiation source and a radiation detector are positioned on opposite sides of the outside surface of the vessel. A positioning system is provided for moving and locating the radiation source and radiation detector longitudinally with respect to the vessel and for moving the radiation source and radiation detector circumferentially with respect to the vessel. In operation, the positioning system causes the radiation source and radiation detector to spiral along the vessel in a coordinated manner while the radiation source illuminates an adjacent region of the vessel with radiation. The radiation is converted into corresponding electrical signals used to generate images of objects in the radiation path. Finally, an operator inspects the images for defects.

9 Claims, 3 Drawing Sheets

HIGH SPEED DIGITAL RADIOGRAPHIC INSPECTION OF PIPING

FIELD OF THE INVENTION

This invention relates generally to high-speed radiographic inspection of pipelines or other fluid transport vessels. Pipelines or vessels that transport fluid products such as natural gas, crude oil, and other chemical and petroleum products are subject to damage due to physical forces applied to them, and due to chemical and electrolytic action. To assure that a vessel is safe for continued operation it is periodically inspected for flaws by nondestructive testing or inspection apparatus.

BACKGROUND OF THE INVENTION

Throughout the following specification, the term vessel collectively includes, but is not limited to, a pipeline, pipeline section, column, column section, heat exchanger silo, and heat exchanger silo section; and, unless otherwise specified, aspects of the invention are applicable both to pre-installation quality assurance testing as well as to post-installation vessel fault, defect, and anomaly detection.

In order to maintain substantial fluid flow through a fluid transport vessel, internal vessel characteristics need to be monitored so that defects, obstructions, and other anomalies in the vessel can be detected and repaired efficiently, or in the case of quality assurance testing, discarded. In addition to manufacturing defects and other anomalies, such as obstructions, affecting fluid flow in the vessel, stresses imposed on the vessel in response to changes in fluid pressure can lead to structure fatigue and crack formation. Frequently, companies must endure substantial monetary costs and schedule delays due to the detection and repair of these vessel anomalies.

In order to satisfy processing requirements, minimize energy losses and increase worker safety, it is often desirable to attach an external layer of thermal insulation around the outside diameter of individual fluid transport vessels. As discussed in more detail below, the insulation layer tends to complicate the vessel inspection process, making it difficult to obtain fast and accurate information about vessel defects, such as corrosion under insulation, situated underneath the protective layer of insulation. Accordingly, prior inspection methods have not been entirely satisfactory in detecting vessel defects, while minimizing inspection costs and scheduling delays.

The detection of defects in vessels has been made by resorting to different solutions, for example ultrasonic inspection systems, where an internal invasive device crawls the length of the vessel while emitting ultrasonic probing pulses towards the vessel wall and receiving the reflected ultrasonic pulses in order to inspect the vessel wall for anomalies. This crawling device, typically referred to as a "pig", poses a serious blockage to the normal fluid flow through a vessel and may require several days for the inspection of a lengthy vessel, decreasing vessel output capacity and production. Furthermore, the amount of data a pig can record, the life of its battery, and the wear of its components from crawling the vessel all limit the usefulness of the pig.

In a typical pulse-echo type of ultrasonic inspection system, an electronic signal generator is provided which generates pulses or periodic wave trains and a sending transducer responds thereto to emit a burst of ultrasonic energy. A couplant is required to transfer energy from the sending transducer to the test piece. A receiving transducer is provided to receive and convert energy reflected back on the interior of the test piece and develop corresponding electrical signals. In many cases, the same transducer is used as both a sending transducer and a receiving transducer. When a separate receiving transducer is provided, a couplant is required between it and the test piece. A display or indicating device, typically a cathode ray tube, is associated with the detector means to produce indications of reflections from internal flaws in the test piece.

Another conventional ultrasonic inspection approach is measuring the acoustic signature of a vessel to detect vessel anomalies. This technique sometimes involves hitting the vessel on its side with a hard object, such as a hammer, and then measuring the acoustic signature of the vessel. Anomalies often alter the acoustic signature of a vessel as compared to a vessel with no such anomalies. However, the magnitude of the anomaly that may be detected is dependent upon the wavelength of the waveform transmitted along the vessel, and sound waves generally have longer wavelengths than some other waveforms. Therefore, this technique typically fails to detect smaller-sized anomalies in a vessel and is relatively ineffective in pre-installation quality assurance testing.

It is important to note that the above mentioned ultrasonic inspection systems have not been entirely satisfactory with respect to the inspection of insulated vessels. For example, it is known that the amount of energy reflected at an interface between two media is a function of differences in the acoustic impedances in the two media. Since there is a large difference between the acoustic impedances in the insulation layer and that in most solids, especially metal vessels, a very high proportion of the sound wave energy generated by an ultrasonic inspection system is reflected at the vessel-insulation interface, resulting in a very low proportion of energy being transmitted to the ultrasonic detector for the detection of defects. To avoid this unsatisfactory result, the system operator would be required to perform the costly and labor intensive step of removing the protective layer of insulation from the outer surface of the vessel prior to commencing the ultrasonic inspection process.

To overcome this limitation, attempts have been made to attach X-ray equipment to an internal crawling device for the radiographic inspection of a vessel. In contrast to sound waves, X-rays, being electromagnetic waves, are not reflected by the insulation layer surrounding the vessel. To the contrary, X-rays propagate directly through the insulation layer, impinging on an X-ray detector, thereby generating an output signal for the detection of defects. In this way, it is unnecessary to remove the insulation layer from the vessel in order to conduct the X-ray inspection, allowing the inspection system to detect vessel anomalies or "corrosion under insulation" that occur when water or other destructive agents become trapped between the insulation layer and outer surface of the vessel.

One of the disadvantages of this type of X-ray machine is that the wheels tend to climb the tangential sidewalls of the vessel, causing the carriage to rock or overturn while it is traveling through the vessel. Such rocking motion also makes it difficult to properly align the attached radiation detector with the external radiation source as well as making it difficult to locate and position the radiation detector proximate the specific zone under inspection. The failure to maintain proper alignment between the source and detector adversely impacts the quality and accuracy of the inspection data. Moreover, as mentioned above, internal or invasive crawling devices pose a serious blockage to the normal fluid flow through a vessel, decreasing vessel output capacity and production.

Attempts have also been made to attach X-ray equipment to external crawling devices for the radiographic inspection of a pipe. For example, U.S. Pat. No. 5,698,854 entitled METHOD AND APPARATUS FOR INSPECTING PIPES, discloses an external X-ray scanning device that moves along the axial direction of the pipe while emitting X-ray radiation toward a plurality of detectors arranged on the opposite side of the pipe, for measuring the thickness of a pipe without the insulation being removed. However, the apparatus is not adapted to easily traverse past pipeline intersections, nor is the system capable of inspecting complex vessel structures such as heat exchangers, as discussed in more detail below.

Another approach to vessel inspection that has been proposed involves the use of radiographic film to capture images of the vessel. Such systems typically require large amounts of film, and are relatively slow since the film must be removed and developed before the images can be examined. Replacing the film with an X-ray detector is an alternative to X-ray film, but systems of this sort likewise require precise alignment of the X-ray source and detector with respect to each other and the vessel. As mentioned above, precise alignment has been heretofore difficult to achieve, especially given the immense size and length of vessels. Accordingly, it is desirable to produce a system that is capable of providing precise alignment between the source and detector, in a non-invasive manner, for the fast and accurate radiographic inspection of fluid transport vessels.

Another approach to the radiographic inspection of fluid transport vessels proposes the use of digital or CMOS radiation detectors for the inspection system. In view of the danger which radiation presents to the personnel handling the inspection equipment, digital or CMOS detectors are not entirely satisfactory for radiographic inspection systems. For instance, digital or CMOS detectors are relatively insensitive or "hard of hearing", therefore requiring the radiation source to emit relatively high levels of radiation for the generation of a detectable output signal. Accordingly, it is desirable to produce a radiographic inspection system that does not require such high levels of source radiation in order to generate a detectable output signal.

Turning now to the X-ray inspection of hollow fluid transport vessels, standard two-dimensional X-ray images are generally sufficient to expose any structural defects or faults in the outer vessel wall surface. On the other hand, for more complex inspection requirements, such as for the inspection of the internal structure of heat exchanger vessels, such two dimensional images have well-known limitations. For example, with standard X-rays, the constructed image shows every surface in the X-ray path projected onto a flat plate. This makes it hard to study or inspect in great detail the independent characteristics of individual components or objects in the X-ray path. Moreover, with standard X-ray techniques, one has a limited choice of viewing angles; thus, it is not feasible to obtain an elemental cross-sectional view of the vessel under inspection.

The limitations of standard X-ray imaging have largely been overcome through the development of a Computed Tomography (CT) or CT scanning technology. A conventional X-ray CT scanner system generally comprises: an X-ray tube for radiating a flat, fan-shaped X-ray beam; and an X-ray detector arranged in opposition to the X-ray tube for the detection of the X-ray beam; and either a gantry to which the source and detector are attached to rotate about the object in question, or a part manipulator which has of a rotation table which can rotate the part, leaving the source and detector stationary. The object to be scanned is placed between the X-ray tube and the X-ray detector, and the X-ray tube and the X-ray detector are rotated in the same direction and at the same angular velocity, with the object as the center of rotation. During the rotation, X-ray projection data representing various-direction images of the object is collected on the basis of the X-rays detected by the X-ray detector. After the X-ray projection data is collected in a sufficient amount, it is analyzed by a computer to calculate the X-ray absorption coefficient at each voxel (volume element) in a plane slicing the object. In accordance with the absorption coefficient voxel data, a format suitable for rendering and/or analysis is produced such as gray scale or false color image.

In general, X-ray CT technology has achieved widespread use in the medical field for collecting X-ray projection and diagnostic data with respect to a patient being examined. The technology has met with more limited application in industry, especially with respect to the inspection of heat exchanger and other fluid transport vessels. Accordingly, it is desirable to produce a system that is capable of detecting the internal characteristics of relatively simple hollow fluid transport vessels and of relatively complex heat exchanger vessels in a non-invasive manner. It is also desirable to inspect insulated vessels in a fast, continuous, and cost effective manner, as well as to accurately detect smaller-sized anomalies in fluid transport vessels.

The foregoing has outlined a need for an improved system for the inspection of hollow fluid transport vessels as well as for the inspection of relatively more complex heat exchanger vessels. It is therefore desirable to have a fast, accurate, safe, and cost effective inspection system that is capable of detecting, in a non-invasive manner, detailed internal characteristics of fluid transport and heat exchanger vessels with minimal vessel production downtime.

SUMMARY OF THE INVENTION

The present invention provides a system and method for high-speed radiographic inspection of fluid transport vessels in which a radiation source and a radiation detector are located outside of the vessel, preferably positioned on opposite sides of the vessel. The present invention also provides a positioning system for moving the radiation source and the radiation detector in a coordinated manner longitudinally and circumferentially with respect to the vessel under inspection. In operation, motive means are provided to move the radiation source and radiation detector around the vessel, by way of example but not by way of limitation, in a helical pattern while the radiation source illuminates an adjacent region of the vessel. The radiation is converted into corresponding electrical signals used to generate images of objects in the radiation path. Finally, an operator inspects the images for defects.

The present invention and its advantages over the prior art will become apparent upon reading the following detailed description and the appended claims with reference to the accompanying drawings.

DETAILED DESCRIPTION OF THE INVENTION

Figure 1:
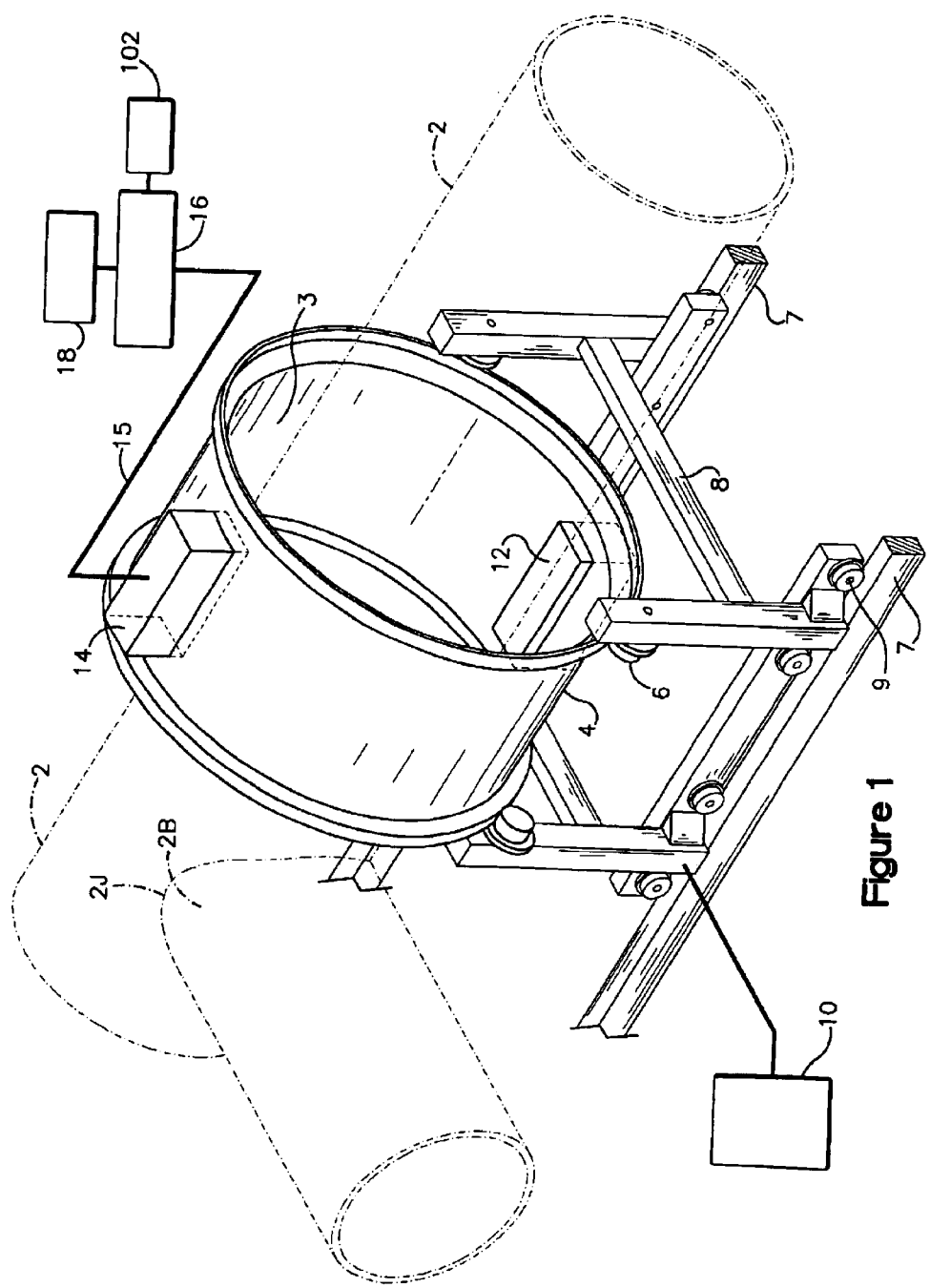
FIG. 1 is a perspective view of the radiographic inspection system for the inspection of fluid transport vessels.

Referring to the drawings wherein identical reference numerals denote the same elements throughout the various views, FIG. 1 schematically shows a radiographic inspection system 100 for the inspection of fluid transport vessels 2. As mentioned above, the term vessel collectively includes, but is not limited to, a pipeline, pipeline section, column, column section, heat exchanger silo, and heat exchanger silo section; and, unless otherwise specified, aspects of the invention are applicable both to pre-installation quality assurance testing as well as to post-installation vessel fault, defect, and anomaly detection.

As best shown in FIG. 1, the inspection system 100 generally comprises a set of at least two carriage guide rails 7 positioned parallel to the longitudinal central axis of vessel 2. The system further comprises a carriage 8, slidingly mounted on a set of at least four carriage-rollers 9 which are rotably mounted on the guide rails 7, enabling the carriage to move back and forth along the longitudinal central axis of the vessel under inspection.

Referring again to FIG. 1, the inspection system 100 further comprises a set of at least four wheel-rollers 6 rotably mounted on carriage 8, and an inspection wheel 4 resting on the wheel-rollers, enabling the wheel to be turned circumferentially through a full 360 degree revolution. As best shown in FIG. 1, the inside diameter of the wheel is greater than the outside diameter of the vessel, providing a clearance gap 3, allowing the wheel to slip over the outside diameter of the vessel; the wheel 4 being positioned coaxially thereto, allowing the wheel to circumrotate around the vessel 2 as best shown in FIG. 1.

As best shown in FIG. 1, the system 100 further comprises a radiation source 12 and a radiation detector 14. The radiation source and radiation detector are relatively situated and fixedly mounted on opposite sides of wheel 4 so that in operation, radiation emitted by the radiation source irradiates through the vessel 2 and impinges on the radiation detector, generating an electrical output signal that is indicative of the radiation pulses impinging on the radiation detector.

Referring again to FIG. 1, the system 100 further comprises motive means, such as an electric motor (not shown), to drive the wheel-rollers 6 and carriage-rollers 9, under the control of the controller 10, to thereby turn the wheel 4 circumferentially around the vessel 2 and move the carriage 8 back and forth along the longitudinal central axis of the vessel. In this way, inspection may be performed by moving the wheel circumferentially while the source is illuminating an adjacent region of the vessel, or inspection may be performed by moving the wheel longitudinally while the source is illuminating an adjacent region of the vessel, or the carriage may be moved longitudinally so that one complete circumferential revolution of the wheel is completed in the time required for the carriage to travel longitudinally a distance equal to the scanning width of the radiation detector. In operation, as the radiation source 12 and radiation detector 14 move around the vessel, successive and continuous lines of data may be transmitted by the radiation detector 14 to the imaging unit 16, thereby providing full azimuthal coverage of the vessel under inspection and causing a corresponding image to be generated, in real-time, on display 18.

The radiation source 12 is preferably, but not necessarily, a standard industrial X-ray accelerator tube powered by a high voltage power supply (not shown). As skilled artisans will appreciate, alternative radiation sources, such as an isotopic radiation source producing gamma rays, could be used as well.

The radiation detector 14 can be any means that is capable of converting radiation received from the radiation source 12 into electrical output signals as is known in the art. Many suitable detectors, preferably, but not necessarily, an amorphous silicon detector, are commercially available. Amorphous silicon detectors with a coupled scintillator are preferred because they have the potentially highest Detective Quantum Efficiency (DQE) over other types of digital or CMOS detectors, therefore reducing the relative amount of X-ray energy required to generate a sufficient output signal, and hence clearest and most well defined image. In operation, while the radiation source 12 is emitting radiation, image data signals output by the radiation detector 14 are fed via cable 15 to imaging unit 16 as best shown in FIG. 1.

Referring again to FIG. 1, the imaging unit 16, which can be a conventional computer unit, processes these signals and causes a corresponding image to be generated on image display 18. Here, imaging unit 16 comprises software means to combine and manipulate the signal intensity information derived from the image data signals. Meanwhile, the computer manipulated signal intensity information is calibrated with known benchmark signal attenuation information obtained from industry standard step wedges in a manner known in the art. As a result, accurate readings and measurements of the physical dimensions of objects or defects in the X-ray path can be obtained from corresponding intensity gradients displayed in the X-ray image. State of the art imaging units are shown in U.S. Pat. No. 6,154,516.

With the inspection of vessel networks, for example the inspection of oil refinery vessel systems, a plurality of individual fluid transport vessels typically run together, forming a confluent grid or network of individual vessels. Depending on specific vessel processing requirements, individual vessels may converge together and intersect, from different angles, forming confluent intersections or manifold junctions 2J as best shown in FIG. 1. One limitation of inspection system 100 is shown, for example, where vessel junction 2J is encountered during the inspection process. Here, wheel 4 is blocked from traversing past the vessel junction by the intersecting vessel 2B. As a result, the wheel must be removed from the vessel before the carriage can be moved to the other side of the interfering vessel junction. Once the carriage is moved to the other side of the intersecting vessel 2B, the wheel may be re-attached to the carriage, allowing the inspection of vessel 2 to proceed.

Figure 2:
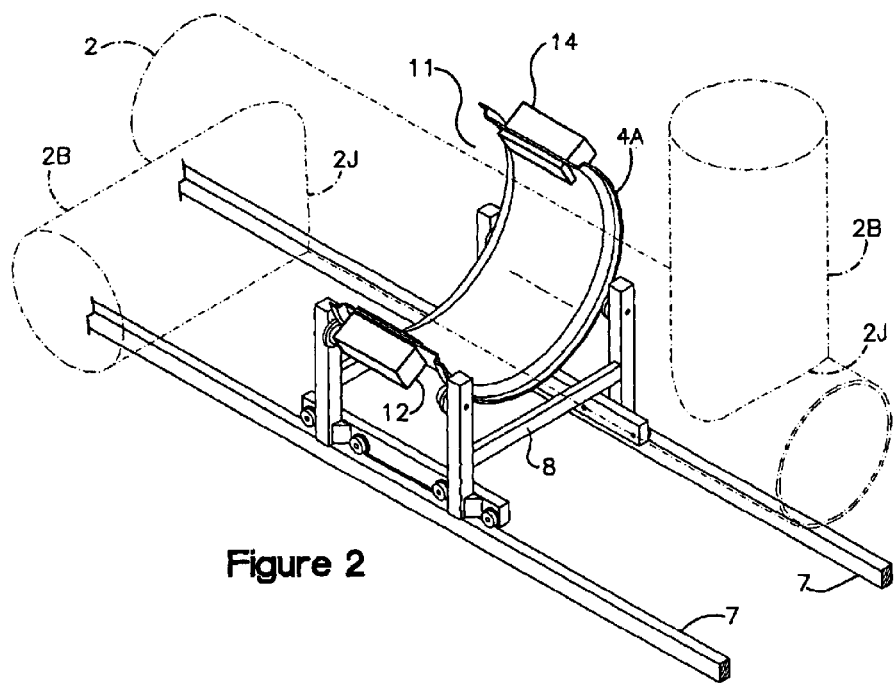
FIG. 2 is a perspective view of an alternative radiographic inspection system equipped with an alternative detector and source mounting system.

To overcome the above limitation, an alternative embodiment is shown in FIG. 2 whereby inspection wheel 4 is replaced by a semi-circular shaped C-ring 4A for use in mounting and locating the radiation source 12 and radiation detector 14 in similar fashion on the carriage 8 and guide rails 7. Here, the semi-circular shape of the C-ring 4A provides a clearance gap 11, which may be suitably aligned with the approaching vessel 2B, allowing the C-ring to traverse past the vessel junction 2J, eliminating the costly and labor intensive step of removing the inspection equipment from the vessel under inspection when a vessel junction or column is encountered during the inspection process.

Figure 3:
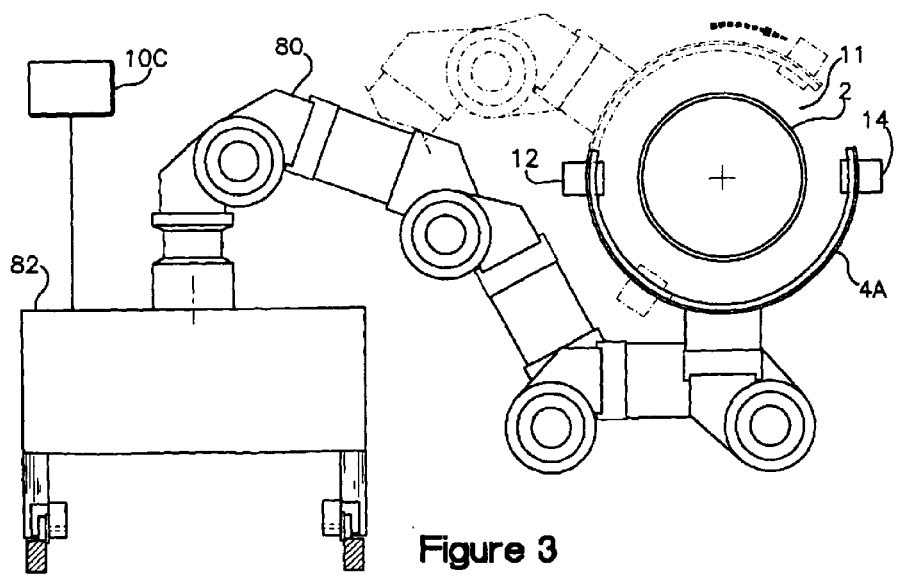
FIG. 3 is an end view of an alternative radiographic inspection system equipped with an alternative positioning system.

Referring now to FIG. 3, there is shown an alternative mounting structure whereby C-ring 4A is alternatively supported and positioned by an articulating robotic or simple C-arm 80. As shown in FIG. 3, the C-arm 80, under the control of the controller 10C, enables the C-ring 4A to move around the vessel to achieve full circumferential coverage of the area under inspection. Furthermore, as shown in FIG. 3, the articulating C-arm 80 is mounted to transport vehicle 82, enabling the C-arm to move back and forth along the longitudinal length of the vessel 2. In this way, under the control of the controller 10C, inspection may be performed by moving the C-ring circumferentially while the source is illuminating an adjacent region of the vessel, or inspection may be performed by moving the C-ring longitudinally while the source is illuminating an adjacent region of the vessel, or the C-ring may be moved longitudinally so that one complete circumferential revolution of the C-ring is completed in the time required for the C-ring to travel longitudinally a distance equal to the scanning width of the radiation detector. In this way, the radiation source 12 and radiation detector 14 move around the vessel to achieve full azimuthal coverage of the vessel under inspection.

The C-arm also allows the operator to do detector calibration with minimal effort. Detector calibration usually consists of taking a series of "dark images", which is a readout of the detector channels for an exposure with a zero flux of X-rays, and a series of "air images" where the detector channels are read out for a known exposure of X-rays with no object between the source and detector. This produces a flat field image which allows the characterization of the response of all the detector channels.

Mobility is another advantage of using a C-ring 4A supported by an articulating C-arm 80 in combination with transport vehicle 82 as shown in FIG. 3. Referring back to the carriage 8 and guide rail 7 transport system as best shown in FIG. 1, the range of longitudinal motion of the carriage is limited by the overall length of the guide rails. As such, during the inspection process, if the carriage reaches the end of the guide rails, the operator is required to interrupt the inspection process and re-locate the carriage and guide rails further down the vessel to continue the inspection process. This approach is repeated until the entire length of the vessel has been inspected. In contrast, transport vehicle 82, for example a truck or trackless vehicle as shown in FIG. 3, enables the inspection equipment to move continuously along the entire length of a vessel, without having to interrupt the inspection process and re-position the inspection equipment. Furthermore, as described above, the clearance gap 11 of C-ring 4A may be suitably aligned, under the control of the controller 10C, to move the inspection equipment in a continuous manner past intersecting columns 2B and junctions 2J without interrupting the inspection process.

Figure 4:
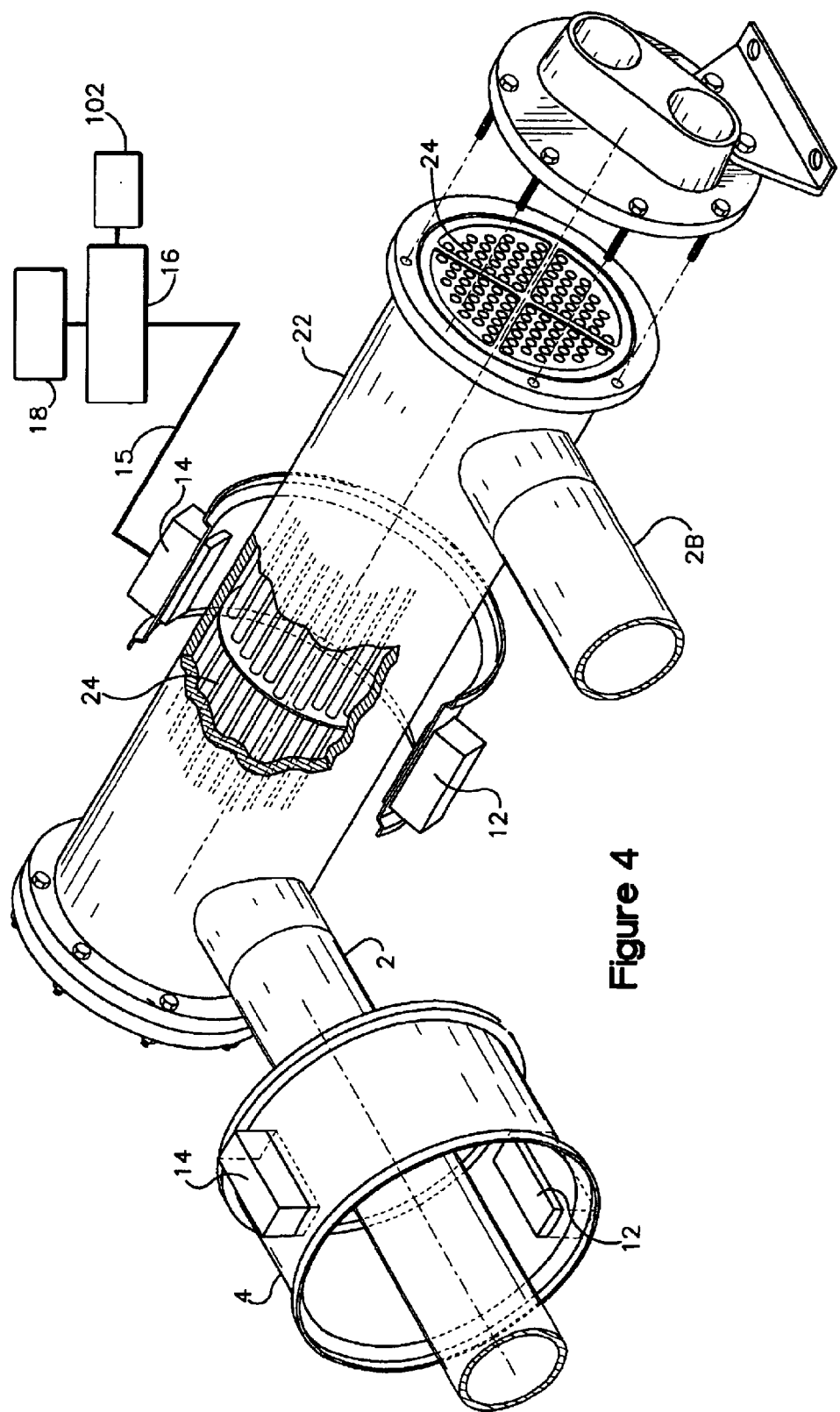
FIG. 4 is a sectional perspective view of a heat exchanger fluid transport vessel.

Referring now to FIG. 4, there is illustrated a heat exchanger 22 in combination with confluent vessels 2 and 2B, ready for inspection. A typical heat exchanger 22 comprises a network of thermally coupled transport straws or tubes 24 designed for the transfer of heat energy between fluids of differing temperatures, by thermodynamic principles, between confluent input and output vessels in a manner known in the art. To obtain quality assurance and fluid processing efficiency, the internal characteristics of heat exchangers 22 need to be monitored so that defects, obstructions, and other anomalies in the vessel structure can be detected and repaired efficiently. Accordingly, in the embodiment shown in FIG. 4, CT software means 102 may be provided, preferably in combination with imaging unit 16, for calculating and manipulating X-ray intensity measurements, and reconstructing detailed three-dimensional CT images of the vessel under inspection as discussed in more detail below.

In operation, as the radiation source 12 and radiation detector 14 sweep around the vessel 2, a sufficient number of X-ray images or projections are acquired so an estimate of the attenuation coefficient per voxel of the object being imaged can be calculated. Typically for our application, one thousand X-ray images or projections are acquired from uniformly spaced incremental angular rotations about the object. The data acquisition of each individual projection image is acquired by means of a radiation detector 14, which converts the X-ray energy from the beam which passes through the vessel to an electrical signal. These signals are transferred to the imaging unit 16 for processing and storage to a computer disk or alternate media. The data is simultaneously displayed on the imaging display 18 in real-time. Once the complete data set of projection images are acquired and stored, they are then manipulated by a resident CT reconstruction software program which characterizes the volumetric structure of the object in terms of the X-ray attenuation coefficient per voxel. There are many different algorithms, the simplest being back projection, developed to accomplish this task, as is well known in the art. The average linear attenuation coefficient along the projected line through the object can be calculated from the measured intensities of the corresponding electrical output signals. Once the CT software has manipulated the measurements from the thousands of recorded X-ray projections, a three dimensional image of the object in the X-ray path may be reconstructed. In this way, it is possible to study and inspect complex structures in three dimensions, including the materials and density distributions of these materials, for structures including, but not limited to, the tubular structure of heat exchangers 22 as shown in FIG. 4. Representative X-ray detection and CT scanner systems that may be used in the invention are disclosed in U.S. Pat. Nos. 6,154,516 and 4,982,415. The disclosures of both of these patents are incorporated by reference herein.

The foregoing has described a radiographic inspection system that provides high-speed digital inspection of fluid transport vessels. The system allows for the inspection of vessel networks and junctions without the removal of vessel insulation and without interrupting the inspection process or the flow of fluid product, thereby realizing substantial time and cost savings over traditional inspection methods. The system also allows for the inspection of heat exchangers or other complex vessels that has heretofore been difficult to achieve.

While specific embodiments of the present invention have been described, it will be apparent to those skilled in the art that various modifications thereto can be made without departing from the spirit and scope of the invention as defined in the following claims.

What is claimed is:

1. A system for high-speed radiographic inspection of a fluid transport vessel, said system comprising:

(a) an X-ray source and a radiation detector, said source being aligned with said detector longitudinally along an outside surface of said vessel, said source and said detector being positioned on opposite sides of said outside surface;

(b) first positioning means for moving said source and said detector longitudinally with respect to said vessel;

(c) second positioning means for moving said source and said detector circumferentially with respect to said vessel;

(d) a controller for controlling said first and said second positioning means said controller causing said source and said detector to move with respect to said vessel in a coordinated manner so that one complete circumferential revolution of said source and said detector is completed in the time required for said detector to travel longitudinally a distance equal to the scanning width of said detector while said source is illuminating an adjacent region of said vessel with X-rays; and (e) a real-time imaging unit wherein said imaging unit receives image data signals from said detector.

2. The system of claim 1 further comprising a display means operatively associated with said imaging unit.

3. The system of claim 1 wherein said first positioning means comprises two guide rails disposed parallel to said vessel, and a carriage slidingly mounted on said guide rails to enable said carriage to move longitudinally with respect to said vessel and wherein said second positioning means comprises roller means rotably mounted on said carrier, and a wheel resting on said roller means to enable said wheel to be turned circumferentially providing full azimuthal coverage with respect to said vessel.

4. The system of claim 3 wherein said wheel is a C-ring, and said second positioning means is an articulating C-arm.

5. The system of claim 4 wherein said first positioning means is a transport vehicle.

6. The system of claim 5 further comprising CT means for converting said image data signals into corresponding three-dimensional CT images of said fluid transport vessel.

7. A method for high-speed radiographic inspection of a fluid transport vessel, said method comprising:

(a) providing an X-ray source and a radiation detector, said source being aligned with said detector longitudinally along an outside surface of said vessel; and (b) causing said source and said detector to move longitudinally with respect to said vessel, wherein said source and said detector are made to move in a coordinated manner with respect to said vessel so that one complete circumferential revolution of said source and said detector is completed in the time required for said detector to travel longitudinally a distance equal to the scanning width of said detector while said source is illuminating an adjacent region of said vessel with X-rays.

8. The method of claim 7 further comprising:

(a) collecting image data signals from said detector; and (b) displaying real-time two-dimensional images generated by processing said image data signals.

9. The method of claim 7 further comprising:

(a) collecting image data signals from said detector; and (b) displaying three-dimensional CT images generated by CT processing said image data signals.

* * * * *